United States Patent [19]
Finnemore et al.

[11] Patent Number: 6,159,189
[45] Date of Patent: Dec. 12, 2000

[54] METHOD FOR INSTILLING A CONTROLLED DOSE OF FLUID INTO THE EYE

[75] Inventors: Victor M. Finnemore, Belmont; Donald R. Korb, Boston, both of Mass.

[73] Assignee: Ocular Research of Boston, Inc., Boston, Mass.

[21] Appl. No.: 09/313,837

[22] Filed: May 18, 1999

Related U.S. Application Data

[63] Continuation-in-part of application No. 09/132,958, Aug. 12, 1998, abandoned.

[51] Int. Cl.[7] .................................................. A61M 35/00
[52] U.S. Cl. ............................................................ 604/294
[58] Field of Search ...................... 604/290, 294; 600/383, 318, 307; 514/912, 15; 424/78.04, 427; 128/898

[56] References Cited

U.S. PATENT DOCUMENTS

| | | | |
|---|---|---|---|
| 3,075,527 | 1/1963 | Bechtold | 604/294 |
| 4,409,205 | 10/1983 | Shively . | |
| 4,540,408 | 9/1985 | Lloyd | 604/294 |
| 5,352,445 | 10/1994 | Lavaux . | |
| 5,884,630 | 3/1999 | Fujishima . | |

OTHER PUBLICATIONS

Lemp MA, Hamill Jr., "Factors affecting tear film break-up-time in normal eyes", *Arch Ophthalmo* (1973) 89:103–105.

Rengstorff, "The precorneal tear film: breakup time and location in normal subjects", *Am J Optom Physiol Opt* 1974; 51–765.

Norn, "Diagnosis of dry eye"; Lemp et al., *The Dry Eye. A Comprehensive Guide*, Berlin: Springer—Verlag, 1992:152, 153, 178.

Tomlinson, "Complications of Contact Lens Wear", St. Louis: Mosby, 1992:169, 205.

Lowther, "Examination of patients and predicting tear film–related problems with hydrogel lens wear", *Dryness, Tears, and Contact Lens Wear*, Boston: Butterworth–Heinemann, 1997:39, 41.

*Primary Examiner*—George Manuel
*Attorney, Agent, or Firm*—Peter F. Corless; Christine C. O'Day; Edwards & Angell, LLP

[57] ABSTRACT

The invention is a test strip and method for delivering a controlled dose of fluid to the eye. The strip and method is useful to determine break-up-time of the tear film over the cornea. The method comprises providing a planar ophthalmic test strip having a length greater than its width and having a tip on at least one of its end. The tip adsorbs liquids, has a width that is less than the width of the remainder of the strip, and has a surface area not exceeding 30 square mm. The tip is wetted with liquid, placed in contact with the corneal surface and break-up-time is observed. The test strip is designed to deliver a limited dose of from 0.5 to 1.0 μl of liquid to the surface of the cornea.

23 Claims, 1 Drawing Sheet

METHOD FOR INSTILLING A CONTROLLED DOSE OF FLUID INTO THE EYE

This application is a continuation-in-part of application Ser. No. 09/132,958 filed on Aug. 12, 1998 now abandoned.

INTRODUCTION

The invention relates to a process and test device for adding a controlled dose of fluid to the eye. In one embodiment, this invention relates to a process for measuring break-up-time (BUT) of a tear film over the corneal surface. More specifically, in the preferred embodiment, the invention relates to a process and device for measuring BUT that is more accurate and reliable than processes and devices previously used.

DESCRIPTION OF THE PRIOR ART

BUT is defined as the time interval following a blink to the occurrence of gaps or breaks in a tear film found on the corneal surface. BUT is therefore a measure of tear film stability.

There are two methods currently used to measure BUT. The method of choice involves addition of sodium fluorescein ("fluorescein") to the tear film. The fluorescein colors the tear film yellow-green and causes the film to fluoresce on exposure to blue light. Observation of the tear film is made using a slit lamp at moderate magnification and a blue filter to provide transmission within a range of from approximately 330 to 400 nm. A relatively wide light beam is used to scan the entire corneal surface. The elapsed time for the development of dark areas in the yellow-green colored fluorescent tear film following a blink is termed BUT. A BUT of about 10 seconds is considered normal; 5 to 10 seconds abnormal; and less than 5 seconds indicative of dry eye syndrome; Lemp MA, Hamill Jr., "Factors affecting tear film break-up-time in normal eyes", *Arch Ophthalmo* (1973) 89:103–105; Rengstorff, "The precorneal tear film: breakup time and location in normal subjects", *Am J Optom Physiol Opt* 1974; 51–765; Norn, "Diagnosis of dry eye"; Lemp et al., *The Dry Eye. A comprehensive Guide*, Berlin: Springer-Verlag, 1992:152, 153, 178; and Tomlinson, "Complications of Contact Lens Wear", St. Louis: Mosby, 1992:169, 205, each incorporated herein by reference.

The BUT test using fluorescein has been the standard method for evaluating tear film stability since about 1969. Though the method was initially termed BUT, currently the method is often referred to as fluorescein-break-up-time (FBUT) to distinguish it from an alternative method used to measure BUT.

The second method used to measure BUT is a non-invasive test (NIBUT) introduced in 1985. The NIBUT test uses the principal of reflection from the tear layer covering the corneal surface. A grid pattern is imaged onto the tear layer over the cornea and observed at low magnification. The quality of the reflected image is dependent upon the tear film's role and function in providing a smooth optical surface by masking the biological irregularities on the surface of the cornea. The elapsed time following a blink to the first change (disruption) in the image is recorded as the BUT. Because of the complexity involved in performing this test, the NIBUT method is used to a lesser extent than the fluorescein method.

For the FBUT procedure, there are various ways by which fluorescein is applied to the eye. A common method uses a fluorescein sodium ophthalmic paper strip—i.e., a paper strip impregnated with about 1 mg of dry sodium fluorescein. The strip measures 5 mm in width by 15 mm in length. In use, the fluorescein strip is wetted with sterile saline prior to application to the eye to dissolve the fluorescein. One recommended method for use of the fluorescein strip is given by Lowther, "Examination of patients and predicting tear film-related problems with hydrogel lens wear", *Dryness, Tears, and Contact Lens Wear*, Boston: Butterworth-Heinemann, 1997:39, 41, incorporated herein by reference.

Fluorescein may also be added to the eye by application of a liquid drop. A digital micropipette is used to apply 1 to 2 μl of fluorescein liquid directly to the eye. A procedure for adding liquid fluorescein to the eye is given by Nelson, "Diagnosis of keratoconjunctivitis sicca", *Int Ophthalmol Clin* 1994;34:37–56, incorporated herein by reference.

Whether fluorescein is added to the eye using a fluorescein strip or as a liquid drop, current procedures often fail to control the volume of fluorescein and therefore, it is difficult to obtain reproducible results. In this respect, it is known that the most accurate and repeatable results are obtained if 1 μl of liquid fluorescein is added as a liquid drop; Marquardt et al., "Modification of tear film break-up time test for increased reliability presented in Holly FJ, ed. *The Precorneal Tear Film in Health, Disease, and Contact Lens Wear*. Lubbock, Tex.: Dry Eye Institute, 1986:57–63. In their study, the authors compared the fluorescein impregnated strip method to the addition of 1 and 2 μl of liquid fluorescein using the micro pipette and found a significant increase in reliability with the 1 μl technique. However, applying a drop of fluorescein to the eye in a volume of 1 μl is difficult and current practice recommends the use of 2 μl as it is a volume more easily controllable. However, even with a dose of 2 μl, the clinician or research scientist must be particularly skilled in the use of the technique and the clinical subject must be cooperative. Thus, the application of micro volumes of fluorescein is technically difficult and therefore not a practicable clinical technique. The use of a fluorescein strip is also not reliable. The strip is wetted with saline and based upon the procedure used, uncontrolled amounts of fluid are added to the eye. In addition, some researchers concluded that contact of a paper strip with the eye disrupted the tear film thereby shortening BUT time.

BUT is an important tool to the clinician and to the researcher and the FBUT test is the primary method for measuring tear film stability. However, though the FBUT test is currently the test of choice for tear film diagnosis, the practitioner considers the test inaccurate and not reproducible. In this respect, a survey in 1998 of 68 of the world's leading practitioners and researchers in tear film found that the FBUT test was used by only 19% of the respondents, Korb, "A Survey of 68 Renowned Practitioners for Preferred Diagnostic Tests for Dry Eye", Presented at British Contact Lens Association $22^{nd}$ Annual Clinical Conference, Brighton, England, May 28, 1998. Transactions in Press. Thus, at present there is no clinically reliable or acceptable method for applying micro amounts of fluorescein to the tear film for the BUT test. Consequently, an improved procedure for administration of the BUT test is needed.

SUMMARY OF THE INVENTION

The subject invention provides a new method for applying a controlled dose of any fluid to the eye and is especially useful for adding fluorescein for the FBUT procedure. The new method is reliable and reproducible, does not require a digital pipette or other costly equipment, and does not use a strip that disrupts the tear film as a consequence of contact with the cornea or the method of use. The subject method recognizes that the accuracy and reproducibility of the FBUT test is dose dependent and that a volume of 0.5 to 1 μl of fluorescein at a concentration of about 2% provides an accurate and repeatable method for quantifying tear film BUT.

The invention of the subject application is based upon modification of an impregnated strip, such as the existing fluorescein impregnated strip, whereby the dose is controlled and the impregnated strip can be applied to the eye without disruption of the tear film and with minimal sensation to the patient. The invention is based upon redesign of the tip of the standard fluorescein strip and application of the redesigned tip to the surface of the eye. The redesign involves an alternative tip shape with a substantial reduction in surface area. In this respect, it has been found that a surface area in the range of from 1 to 30 square mm and preferably, a surface area of 1.5 to 10 square mm provides optimal results. By reduction in the surface area of the tip, a controlled and acceptable volume of a fluid such as fluorescein may be added to the eye without disrupting the tear film.

DESCRIPTION OF THE PREFERRED EMBODIMENTS

Figure 1:
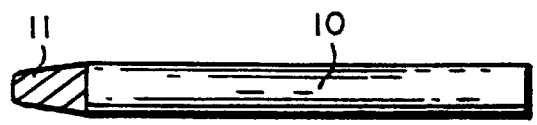
FIG. 1 of the drawings represents a standard fluorescein strip.

The standard fluorescein strip is shown in FIG. 1 of the drawings where the strip 10 has tip 11 saturated with fluorescein. Tip 11 is approximately 5 mm wide and 15 mm long resulting in a surface area of about 75 square mm. When wetted with saline, it has been found that the standard strip delivers between 3 and 20 μl of liquid to the eye dependent upon how the strip is moistened, thereafter shaken, and how much of the surface area of the tip is touched to the ocular surface. In standard practice, it is impractical to moisten a portion of the fluorescein strip with a limited volume of sterile saline in order to limit the amount of fluid delivered to the eye. This approach would require a precision micro volume delivery system and would result in poor control of the fluorescein strip and its application would prevent accurate and reproducible results.

When redesigning the fluorescein strip, the strip of FIG. 1 was altered by change in shape and sized to determine the best means for of delivering 0.5 to 1.0 μl of liquid fluorescein to the eye. It was found that the longer the strip, the more variable the volume of fluorescein retained on the strip after the strip had been moistened with saline. It was further found that the ideal length of the tip of the strip was between 1 and 10 mm and more preferably, between 1.5 and 5 mm. The ideal width for the strip was found to be from 0.5 to 3.5 mm and more preferably, between 1.0 and 2.0 mm. Within the bounds set for these dimensions, it was further found that the total surface area of the tip should vary between 1.0 and 30 square mm and more preferably, within a range of 1.5 to 10 square mm. If the surface area is in excess of 40 square mm, more than the desired amount of fluorescein is delivered to the eye and the clinical results are variable. If the surface area is less than 1.5 square mm, the volume of fluorescein delivered to the eye is frequently inadequate to provide the fluorescence required for the FBUT test.

Figure 2:
FIGS. 2 to 4 of the drawings represent modified strips in accordance with the invention.

One embodiment of a delivery strip in accordance with the invention is illustrated in FIG. 2 of the drawings. The strip 20 has tip 21 attached. The strip shown in FIG. 2 was prepared from a fluorescein impregnated strip manufactured by Chauvin Pharmaceuticals Ltd. of Essex, England by reducing the approximate 15 mm length to approximately 5.0 mm the 5 mm width to 2.0 mm. In this way, the surface area of the tip was reduced to 10 square mm. Thus, over 85% of the surface area of the standard fluorescein strip were eliminated. By reduction of the tip as shown in FIG. 2, the tip is visually differentiated from the remainder of the tip facilitating use of the strip by the clinician by contact of the corneal surface with only the tip portion of the strip. The strip is used in a manner similar to the fluorescein strip of the prior art. A volume of 0.5 to 1.0 μl of liquid fluorescein or any other liquid can be consistently delivered to the tear film by moistening the strip having a tip designed as shown in FIG. 2 with one drop of sterile saline. The wetted strip is then gently shaken in a 1–2 inch vertical plane. The tip of the strip is then applied to the eye.

Figure 3:
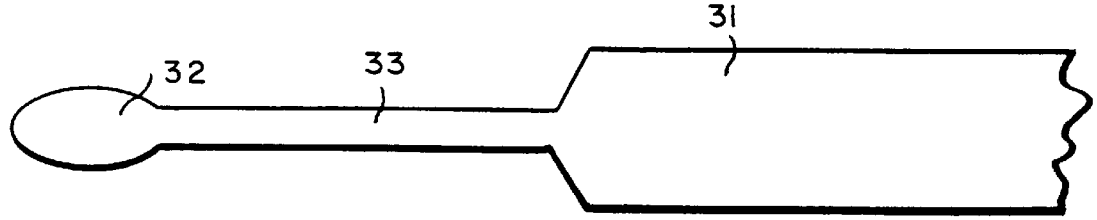
Figure 4:
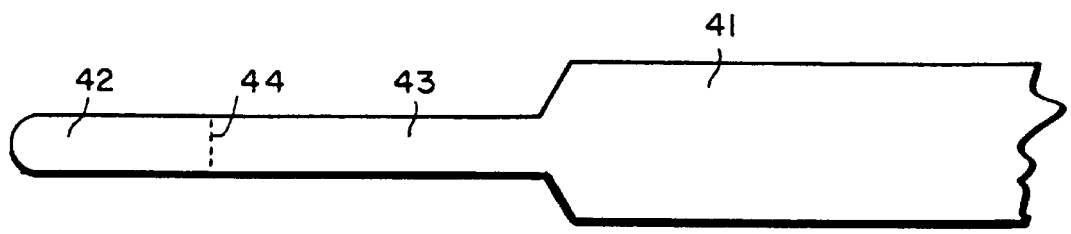

Shaking the strip to remove excess fluid as described above adds an additional variable to dosage control as the degree of shaking can determine the amount of liquid remaining on the strip. FIGS. 3 and 4 of the drawings illustrate preferred strips of the invention as they may be used without shaking the strip to remove excess liquid. The strip of FIG. 3 comprises holder 31, desirably formed from a rigid material such as rigid plastic, and applicator tip 32 illustrated as elliptical. The applicator tip illustrated has a length of 1.75 mm and a width of 1.25 mm for a total surface area of approximately 2 square mm. The holder 31 and applicator tip 32 are separated by porous segment 33 having a length of 6 mm and a width of about 0.6 mm. Separator segment 32 should be of a surface area at least twice the surface area of the applicator tip 32 and preferably at least 4 times the area of the tip. The maximum surface area is not critical. The separator is desirably of a porous material such as porous paper and more desirably, is made of the same material as the applicator tip 32. It has been found that the use of the porous separator segment prevents beading of the fluid on applicator tip 32. If a non-porous separator segment is used, liquid beading may occur on the applicator tip and shaking of the strip will be necessary to remove excess liquid.

An alternative design to that shown in FIG. 3 is illustrated in FIG. 4 of the drawings. The strip again comprises a holder 41 and applicator tip 42. The separator segment 43 is illustrated as an extended portion of applicator tip 42. The width of the illustrated applicator tip and separator segment is 1 mm and the overall length of the two is about 10 mm. In use, only the end portion of the applicator tip 42, the last 3 mm of the illustrated tip, would be wetted with the saline solution. For ease of use by the practitioner, it is desirable to imprint a mark across the porous strip such as that illustrated as 44, to identify that portion to be wetted with saline.

A further goal of the invention is to achieve an applicator tip having adequate flexibility and softness so that when the strip is applied to the eye, it will minimize or eliminate ocular sensation and thus prevent reflex tearing. Even minimal sensation can result in tearing which destabilizes the tear film.

Though the applicator strip has been discussed primarily in terms of application of fluorescein to the eye, it should be understood that essentially any liquid can be added to the eye in controlled volume using the applicator strip defined herein. Consequently, the invention described contemplates application of any liquid to the eye in a controlled dosage.

Figure 5:
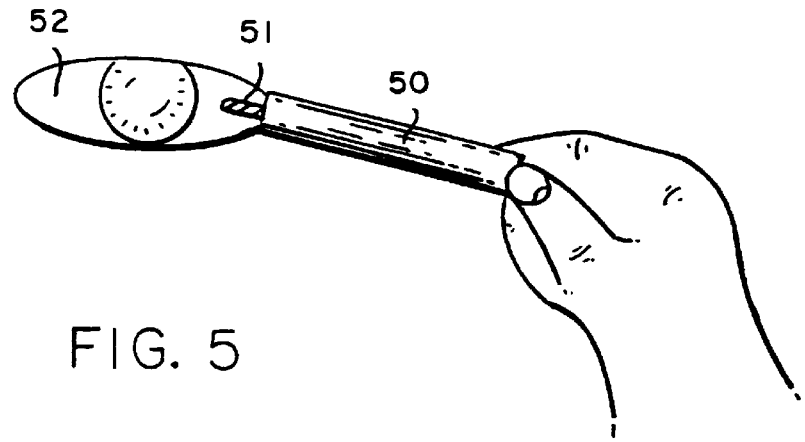
FIG. 5 of the drawings represents application of the strip of FIG. 2 to the surface of the eye.

The method of application of the strip of the invention is shown in FIG. 5 of the drawings where strip 50 has its tip 51 applied directly to the cornea 52. The ability to deliver a micro volume of liquid utilizing the strip having a reduced surface area tip is the combined result of the following factors:

1. Excess fluid falls off of the strips' small surface area after it is moistened, since the smaller the surface area, the less fluid will be retained.
2. The application of the small surface area of the strip to the eye assures consistent delivery of liquid, even by inexperienced personnel after brief training.
3. Because the small area of the strip tip and the rigidity characteristics induce almost no sensation when applied to the eye, the ocular tearing response is minimal.

Using several in-vitro and in-vivo methods, the volume of fluorescein delivered to the eye using the modified fluorescein strip of the invention was compared to the amount delivered with a laboratory Ultra Micro digital pipette. The comparison established that essentially identical fluid volumes of 0.5 to 1 $\mu$l using both techniques. The characteristics of the fluorescence after instillation on the eye were also equal for both techniques. The fluorescein clearance test, as modified by Pflugfelder et al., Epstein-Barr virus infection and immunologic dysfunction in patients with aqueous tear deficiency, *Ophthalmology* 1990, 97:313–23, provided confirmation. The most convincing demonstration of consistent volumes and concentration delivered by the modified fluorescein strip, however, was the essentially identical time periods during which the eyes fluoresced adequately for FBUT evaluation with both the modified strip and liquid volume techniques. Adequate fluorescence for FBUT observation usually started immediately after instillation and lasted for 2 to 5 minutes for both techniques. The length of time for tear film fluorescence is a function of the volume and concentration of the fluorescein. Since the longitudinal fluorescence times were the same for both the reduced size fluorescein strips and the liquid volumes of 0.5 to 1.0 $\mu$l, the volumes and concentrations of the fluorescein delivered to the eye by both methods were necessarily the same. Thus, the modified fluorescein strip technique duplicates the micro digital pipettes' ability to deliver micro volumes of fluorescein providing a clinically applicable method of evaluating BUT and tear film stability in a reproducible manner.

The following protocol was used for clinical evaluation of the fluorescein strips of the subject invention.

The purpose of the tests was to compare the accuracy and reproducibility of a fluorescein strip having a tip reduced in size. In the first series of experiments, the tip reduced was to 2 mm wide by 5 mm long (providing a surface area of 10 square mm). This was compared to the standard size strip having a tip 5 mm wide by 15 mm long (providing a surface area of 75 square mm) in a randomized contralateral study. An additional study population participated in a randomized contralateral crossover study design. A further purpose was to compare the ability of each method in classifying the status of the tear film as dry, borderline (marginal or questionable), or adequate.

Fluorets brand of fluorescein sodium ophthalmic strips as manufactured by Chauvin Pharmaceuticals Ltd., of Essex England, were used for the tests. These fluorescein strips were impregnated with approximately 1 mg of fluorescein sodium USP. The portion of the fluorescein strip which is designed to deliver the fluorescein to the eye after moistening with sterile saline measured approximately 5 mm wide by 15 mm long, providing a surface area of approximately 75 square mm. The fluorescein strip is provided by the manufacturer in sterile individual paper packages. The fluorescein strip is designed to be used on only one eye, and then discarded. A second fluorescein strip is used for the second eye. For this study, the fluorescein strip was used as provided by the manufacturer for one eye. A modified fluorescein strip, reduced in size from 5 mm wide by 15 mm long to 2 mm wide and 5 mm long, reducing the total surface area from approximately 75 square mm to 10 square mm, was used for the second eye. The reduction in size was made with a surgical scissors using aseptic technique.

The method for measuring FBUT was the method recommended by Nelson in Diagnosis of keratoconjunctvitis sicca, *Int Ophthalmol Clin* 1994, 34:37–56, incorporated herein by reference, for the study of the conventional (standard) fluorescein strip since it has also been chosen as the method of choice for FBUT measurement in other contemporary studies. The method includes a step of shaking the strip subsequent to the addition of the sterile saline. In addition to the measurements conducted after waiting 1 minute as recommended by Nelson, three additional measurements were made immediately after instillation of the fluorescein. The time required to initiate the first measurement after the instillation of fluorescein varies between 10 and 20 seconds, which is the time being required to place the patient in the appropriate position in the instrument.

The primary study design was a randomized contralateral eye design. The conventional fluorescein strip was evaluated on one eye, and the modified fluorescein strip on the contralateral (second) eye. The choice of the conventional or modified fluorescein strip for right or left eye was randomized. Six trials were completed for one eye prior to commencing evaluation of the contralateral eye.

The first series of three trials were performed immediately after the instillation of the fluorescein, requiring 10–20 seconds for patient positioning. The trials usually commenced as described 10 to 20 seconds after the instillation of the fluorescein. The three trials were performed consecutively. Between each trial, the patient was first asked to close the eyes and then keep the eyes open as recommended by Nelson. If the BUT reached 20 seconds in duration, the measurement was terminated since the goal was to evaluate the accuracy and reproducibility of the two methods for the range of values required to classify the FBUT values as indicating a dry eye (0–4 seconds), a borderline (marginal or questionable) tear film (5–9 seconds), or an adequate tear film (over 10 seconds). The usual time for starting the second series of 3 measurements was 60–90 seconds after the first instillation. (No further fluorescein was instilled for the second series of three measurements.)

After completion of the first eye, the evaluation of the second eye was made utilizing the same protocol, varying only the type of fluorescein strip. The choice of order of testing for the two different types of fluorescein strips was selected by randomization.

Randomized contralateral crossover studies were conducted with 5 subjects to evaluate whether the results were repeatable if the conventional and new type of strips were evaluated not only on the eye chosen by the randomization process, but also on the other eye (the selection reversed). These randomized contralateral crossover studies were conducted after a rest period of 1½ to 3 hours.

A total of 19 subjects were evaluated. A summary of the results is presented in Tables I and II below. Table I summarizes the results for the 5 subjects whose FBUT values with the standard fluorescein strip method were very variable and obviously not reproducible. Table II summarizes the results for the 14 subjects who demonstrated reasonably reproducible FBUT values with the standard fluorescein strip method.

TABLE I

Comparison of FBUT Values With The Standard And Modified Fluorescein Strips For Subjects With Non-reproducible FBUT Values With The Standard Fluorescein Strip.

| FBUT Classification | Subject # | Standard Fluorescein Strips | | New 2 mm by 5 mm Fluorescein Strips | |
|---|---|---|---|---|---|
| | | Data for each of 3 trials in seconds | Average of 3 trials in seconds | Data for each in 3 trials in seconds | Average of 3 trials in seconds |
| 0–4 seconds (dry eye) | 15 | 2, 8, 1 | 2.66 not reproducible | 8, 10, 11 | 9.66 reproducible |
| 5–9 seconds borderline (marginal or questionable) tear film | 16 | 2, 14, 5 | 7.0 not reproducible | 12, 10, 11 | 11.0 reproducible |
| 10–20 seconds (adequate tear film) | 17 | 10, 6, 14 | 10.0 not reproducible | 19, 16, 20 | 18.33 reproducible |
| | 18 | 18, 8, 6 | 10.66 not reproducible | >20, >20, >20 | >20.0 reproducible |
| | 19 | >20, 17, 10 | 15.66 not reproducible | >20, 18, >20 | >20.0 reproducible |

Table I compares the FBUT values found with the standard fluorescein strip to those found with the new fluorescein strip for the 5 subjects whose FBUT values were not reproducible with the standard strip. The measurements are for the first series of trials, conducted immediately after the instillation of the fluorescein as described in the protocol section. The results of the second series of trials conducted one minute after fluorescein instillation, were equivalent to the first series of trials, and therefore are not included.

The data for each of the three trials listed individually in Table I provides a perspective of the large variability between the three trials. The measurements in three consecutive trials were considered reproducible if the maximum difference in a series of three consecutive measurements (trials) did not differ by more than 3 seconds or by more than a factor of 25%. All 5 subjects did not meet these criteria when the FBUT values from the standard fluorescein strip method were used, but did meet these criteria when the FBUT values found with the modified fluorescein strip were used. An example was subject no. 16, whose FBUT findings when the standard fluorescein strip was used were 2, 14 and 5 seconds. When the new 2 by 5 mm fluorescein strip was used the findings were very reproducible and were 12, 10 and 11 seconds. The absolute values of the fluorescein break-up-times were much longer with the new fluorescein strip method. Although averaging data with large deviations is a questionable practice, it was utilized to offer a comparison of the averages for the three trials by the standard and new fluorescein strip methods. The comparison of the averages for the three trials shows a marked and obvious increase in the average values when performed with the new method; for example from 2.66 to 9.66 seconds (subject no. 15), from 7.0 to 11.0 seconds (subject no. 16), and from 10.66 to over 20 seconds (subject no. 18).

The results with the 5 subjects whose FBUT values with the standard fluorescein strips were not reproducible establish that for a series of three trials conducted with the modified strip, immediately after instillation of the fluorescein, the results were accurate and reproducible. The results of the second series of three trials conducted one minute after fluorescein instillation were equivalent. The results with the standard method were not accurate or reproducible in either series of measurements conducted immediately after the instillation of fluorescein, or in the second series conducted one minute later. Thus, the new method may be used immediately after instillation of the fluorescein or after 1 or 2 minutes. The elimination of the usual waiting period of one minute prior to conducting the FBUT is a very important clinical advantage. In addition, significantly greater FBUT values were found with the modified method indicating that the condition of the tear film was not as severe as diagnosed by the standard method. These results confirmed the model and hypothesis that if a greater volume of fluorescein is instilled, the greater the disruption to the tear film and the greater the artificial reduction of the FBUT values.

TABLE II

Comparison of FBUT Values With The Standard And Modified Fluorescein Strips For Subjects With Reproducible FBUT Values With The Standard Fluorescein Strip.

| FBUT Classification | Subject # | Standard Fluorescein Strips Average of 3 trials in seconds | New 2 × 5 mm Fluorescein strips Average of 3 trials in seconds |
|---|---|---|---|
| 0–4 seconds (dry eye) | 1 | 1.33 | 2.66 |
| | 2 | 1.33 | 5.33 |
| | 3 | 2.33 | 4.66 |

TABLE II-continued

Comparison of FBUT Values With The Standard And Modified Fluorescein Strips For Subjects With Reproducible FBUT Values With The Standard Fluorescein Strip.

| FBUT Classification | Subject # | Standard Fluorescein Strips Average of 3 trials in seconds | New 2 × 5 mm Fluorescein strips Average of 3 trials in seconds |
|---|---|---|---|
| | 4 | 2.66 | 11.0 |
| | 5 | 3.33 | 7.66 |
| | 6 | 3.66 | 6.66 |
| | | Average = 2.44 | Average = 6.43 |
| 5–9 seconds borderline (marginal or questionable) tear film | 7 | 5.0 | 7.0 |
| | 8 | 5.33 | 7.0 |
| | 9 | 6.33 | 7.66 |
| | 10 | 7.33 | 15.66 |
| | | Average = 6.0 | Average = 9.33 |
| 10–20 seconds (adequate tear film) | 11 | 10.66 | 10.66 |
| | 12 | 10.66 | 12.66 |
| | 13 | 12.33 | 12.66 |
| | 14 | 12.33 | 17.0 |
| | | Average = 11.5 | Average = 13.24 |

Table II compares FBUT values found with the standard fluorescein strip to those found with the modified fluorescein strip for 14 subjects whose FBUT values were reproducible with the standard fluorescein strip. Since the measurements met the criteria for reproducibility, only the average of the three trials is presented.

These results with the 14 subjects whose FBUT values with the standard fluorescein strips were reproducible establishes that the new method provided greater FBUT values, indicating that the condition was not as severe as diagnosed by the standard method. Four of the six subjects with dry findings with the standard fluorescein strip would have been misdiagnosed by at least one classification, as would have one of the four in the marginal classification. Thus, the standard method would have inaccurately diagnosed 5 of the 10 subjects whose findings were reproducible but artificially reduced. The results for the second series of measurements conducted immediately after the initial instillation of fluorescein were equivalent to the first series, and are therefore not included. Thus, the modified method may be used immediately after instillation of the fluorescein or after 1 or 2 minutes, providing a very important clinical advantage and eliminating waiting time. Although the findings with the standard fluorescein strip method were reproducible, very low FBUT values would be expected to be consistent and reproducible even if larger volumes of fluorescein were used since this is the result of very poor tear film stability which results in the rapid tear film break-up. However, as observed in the data in Table II, the rapid tear film break-up which is associated with the dry eye state is then further compromised by the excess volume of fluorescein added to the tear film with the standard method, artificially reducing the FBUT values. The results found with the standard fluorescein strip should be viewed as artificially reduced from the more realistic values found with the modified method. Thus, the FBUT values for the standard method and the modified method were 2.44 versus 6.43 seconds for the dry eye category, and 6.0 versus 9.33 seconds for the marginal tear film category.

The modified method of the invention yielded accurate and reproducible results for all four series of three individual trials when the eyes were reversed in the second half of the randomized contralateral crossover design study, further indicating the reproducibility of the new method. Table III below presents the FBUT data for the four trials, trials 1, 2 and 3 being conducted immediately after the instillation of the fluorescein, and trials 4, 5 and 6 conducted one minute later. The same six trials were then repeated, but with the eyes reversed, after a rest period of 1½ to 3 hours.

TABLE III

Comparison of FBUT Values With The Standard And Modified Fluorescein Strips for Five Subjects Participating in the Randomized Contralateral Crossover Study

| Subject # | Trial #s | Standard Fluorescein Strips Average of 3 trials in seconds | New 2 × 5 mm Fluorescein strips Average of 3 trials in seconds |
|---|---|---|---|
| 1 | 1, 2, 3 | 1.33 | 2.66 |
| | 4, 5, 6 | 1.66 | 2.66 |
| | 1, 2, 3 reversed eyes | 1.0 | 3.33 |
| | 4, 5, 6 reversed eyes | 1.33 | 2.66 |
| 3 | 1, 2, 3 | 2.33 | 4.66 |
| | 4, 5, 6 | 2.33 | 4.33 |
| | 1, 2, 3 reversed eyes | 2.33 | 4.66 |
| | 4, 5, 6 reversed eyes | 3.33 | 6.0 |
| 10 | 1, 2, 3 | 7.33 | 15.66 |
| | 4, 5, 6 | 7.0 | 18.33 |
| | 1, 2, 3 reversed eyes | 4.66 | 15.33 |
| | 4, 5, 6 reversed eyes | 5.33 | 17.33 |
| 16 | 1, 2, 3 | 7.0 not reproducible | 11.0 |
| | 4, 5, 6 | 7.33 not reproducible | 11.66 |
| | 1, 2, 3 reversed eyes | 6.0 not reproducible | 12.66 |
| | 4, 5, 6 reversed eyes | 14 not reproducible | 12.0 |
| 18 | 1, 2, 3 | 10.66 not reproducible | >20 |
| | 4, 5, 6 | 12.33 not reproducible | >20 |
| | 1, 2, 3 reversed eyes | 7.66 not reproducible | >20 |
| | 4, 5, 6 reversed eyes | 10.0 not reproducible | >20 |

The procedures described above were repeated using 12 subjects and a strip having the configuration of the strip shown in FIG. 4 of the drawings with a tip measuring about 1 square mm in width and about 2 square mm in length. The Nelson process was modified by elimination of the step of shaking following the addition of saline, touching of the bulbar conjunctiva with the strip for 1 to 2 seconds and immediately placing the subject in the slit lamp for FBUT measurement without waiting.

The 12 subjects were broken into three trials. Each trial was performed immediately after installation of the fluorescein. This required 10 to 20 seconds for patient positioning. The three trials were performed consecutively. Between each trial for both the standard and new strip, the patient was first asked to close the eyes and then keep the eyes opened as recognized by Nelson, supra. If the BUT reached 20 seconds in duration, the measurement was terminated since the goal of the test was to evaluate the accuracy and reproducibility of the two methods for the range of values required to classify the FBUT lower case values. After completion of the first eye, the evaluation of the second eye was made utilizing the appropriate protocol for the type of fluorescein strip.

Table IV below compares the FBUT values found with the standard fluorescein strip to those found with the new strip. Table IV provides the FBUT times for each of the 3 trials and the average of the 3 trials in seconds for all 12 subjects. The measurements in 3 consecutive trials were considered reproducible if the maximum difference in a series of three consecutive measurements did not differ by more than 3 seconds or by more than a factor of 25%.

TABLE IV

Comparison of FBUT Values
Standard Fluorescein Impregnated Strip
Versus
New (without shaking) Fluorescein Impregnated Strip

| | Standard Fluorescein Strip | | New Fluorescein Strip | |
|---|---|---|---|---|
| Subject # | FBUT time for each of 3 trials in seconds | Average of 3 trials in seconds | FBUT time for each of 3 trials in seconds | Average of 3 trials in seconds |
| 1 | 3<br>1<br>1 | 1.66<br>misdiagnosis | 7<br>10<br>10 | 9.0 |
| 2 | 2<br>3<br>2 | 2.66<br>misdiagnosis | 9<br>7<br>7 | 7.66 |
| 3 | 2<br>2<br>3 | 2.66<br>misdidagnosis | 7<br>7<br>6 | 6.66 |
| 4 | 3<br>7<br>5 | 5.0<br>misdiagnosis and not reproducible | 19<br>>25<br>>25 | >20 |
| 5 | 2<br>5<br>7 | 4.66<br>misdiagnosis and not reproducible | 10<br>10<br>12 | 10.66 |
| 6 | 2<br>2<br>3 | 2.33<br>same | 5<br>5<br>4 | 4.66<br>same |
| 7 | 2<br>3<br>2 | 2.33<br>Misdiagnosis | 12<br>15+<br>15+ | 15+ |
| 8 | 3<br>3<br>2 | 2.66<br>equal | 3<br>4<br>3 | 3.66<br>equal |
| 9 | 11<br>12<br>12 | 11.66<br>equal | 12<br>15+<br>15+ | 15+<br>equal |
| 10 | 3<br>3<br>3 | 3.0<br>same | 4<br>3<br>3 | 3.33<br>same |
| 11 | 9<br>14<br>10 | 11.0<br>same<br>not reproducible | 9<br>12<br>10 | 10.0<br>same |
| 12 | 3<br>4<br>3 | 3.33<br>Misdiagnosis | 8<br>6<br>8 | 7.33 |
| Average for all 12 subjects. | | 4.41 seconds | | 9.41 seconds |

The FBUT times with the standard strip were not reproducible for 3 of the 12 subjects, a 25% failure rate. The FBUT times with the new strip were reproducible for all 12 subjects. The standard strip resulted in misclassification of the status of 7 of the 12 subjects (subjects 1, 2, 3, 4, 5, 7 and 12). This represents a misclassification rate of over 50%. 4 of the 12 subjects were classified as dry eye when they were borderline or marginal with the new strip (subjects 1, 2, 3 and 12). 2 of the 12 were classified as dry with the standard strip when they were normal with the new strip (subjects 5 and 7). One of the 12 was classified as borderline with the standard strip whereas the subject was found normal with the new strip (subject number 4).

All 12 subjects underwent additional FBUT testing to validate which of the 2 test methods provided accurate results. An Ultra Micro digital pipette was used to deliver 1 $\mu$l volume of fluorescein to the ocular surface. The results with the Ultra Micro digital pipette correlated to the FBUT results obtained with the new strip but did not correlate to those obtained with the standard strip.

In view of the above, it can be seen that the subject invention provides a strip and process for accurate addition of fluid to the eye and which permits accurate and reproducible use of the FBUT test for clinical purposes.

What is claimed is:

1. An ophthalmic test strip for contact with the cornea, said strip being planar with a length greater than its width and having a tip on at least one of its ends, said tip being adsorbent of liquids, having an adsorbed liquid therein for transfer to an eye, having a width that is less than the width of the remainder of the strip, and having a surface area not exceeding 30 square mm.

2. The test strip of claim 1 where the surface area of the tip varies between 1 and 30 square mm.

3. The test strip of claim 1 where the surface area of the tip varies between 1.5 and 10 square mm.

4. The test strip of claim 1 where the strip is made of paper.

5. The test strip of claim 1 where at least the tip of the strip is impregnated with dried treatment solution.

6. The test strip of claim 5 where the treatment solution is fluorescein.

7. The test strip of claim 1 where the width of the tip varies between 1 to 2 mm and the length of the tip varies between 1 and 10 mm.

8. The test strip of claim 7 where the length of the tip varies between 1.5 and 5 mm.

9. The test strip of claim 1 where the surface area of the tip enables transfer of from 0.5 $\mu$l to 1.0 $\mu$l of liquid to the cornea surface.

10. An ophthalmic strip for contact with the cornea, said strip comprising a holder and an applicator tip, said holder being separated from said tip by a separator segment, said applicator tip being planar with a length greater than its width and being impregnated with dried treatment solution, said tip having a surface area not exceeding 30 square mm.

11. The strip of claim 10 where the surface area of the applicator tip varies between 1.5 and 10 square mm.

12. The strip of claim 10 where the width of the tip varies between 1 and 2 mm and the length of the tip varies between 1 and 10 mm.

13. The strip of claim 12 where the length of the tip varies between 1.5 and 5 mm.

14. The strip of claim 10 where the holder is separated from the applicator tip by a porous separator segment.

15. The strip of claim 14, where the separator segment is longer than the length of the tip.

16. A method for determining break-up-time of the tear film over a cornea, said method comprising the steps of providing a planar ophthalmic test strip having a length greater than its width and having a tip on at least one of its ends, said tip being adsorbent of liquids and containing an adsorbed material suitable for measurement of break-up-time, having a width that is less than the width of the remainder of the strip, and having a surface area not exceeding 30 square mm, wetting said tip with liquid, contacting the tip of the strip with the cornea surface and measuring break-up-time.

17. The method of claim 16 including the step of vigorously shaking excess liquid from said tip before application of the tip to the eye.

18. The method of claim 16 where the tip is saturated with dried fluorescein and then wetted with saline.

19. The method of claim 18 where the surface area of the tip varies between 1 and 30 square mm.

20. The method of claim 18 where the surface area of the tip varies between 1.5 and 10 square mm.

21. The method of claim 16 where the surface area of the tip, following saturation with saline and shaking, is sized to transfer from 0.5 to 1.0 $\mu$l of liquid to the surface of the cornea.

22. The method of claim 16 where the width of the tip varies between 0.5 to 3.5 mm and the length of the tip varies between 1 and 10 mm.

23. The method of claim 16 where the tip is touched to the eye without a step of shaking the applicator prior to touching the tip to the surface of the eye.

* * * * *